United States Patent
Jung et al.

(10) Patent No.: US 12,233,229 B2
(45) Date of Patent: Feb. 25, 2025

(54) PERFORATED PLATE MICROSTRUCTURE MODULE

(71) Applicants: INDUSTRY-ACADEMIC COOPERATION FOUNDATION, YONSEI UNIVERSITY, Seoul (KR); JUVIC INC., Seoul (KR)

(72) Inventors: Hyung Il Jung, Seoul (KR); Hui Suk Yang, Seoul (KR); Hyeon Jun Kim, Seoul (KR)

(73) Assignees: INDUSTRY-ACADEMIC COOPERATION FOUNDATION, YONSEI UNIVERSITY, Seoul (KR); JUVIC INC., Seoul (KR)

( * ) Notice: Subject to any disclaimer, the term of this patent is extended or adjusted under 35 U.S.C. 154(b) by 912 days.

(21) Appl. No.: 17/183,056

(22) Filed: Feb. 23, 2021

(65) Prior Publication Data

US 2021/0170154 A1 Jun. 10, 2021

Related U.S. Application Data

(63) Continuation of application No. PCT/KR2019/010876, filed on Aug. 27, 2019.

(30) Foreign Application Priority Data

Aug. 28, 2018 (KR) .................. 10-2018-0101288
Aug. 28, 2018 (KR) .................. 10-2018-0101293

(51) Int. Cl.
*A61M 37/00* (2006.01)

(52) U.S. Cl.
CPC . *A61M 37/0015* (2013.01); *A61M 2037/0023* (2013.01); *A61M 2037/0061* (2013.01); *A61M 2205/0244* (2013.01)

(58) Field of Classification Search
CPC ...... A61M 37/0015; A61M 2037/0023; A61M 2037/0061
See application file for complete search history.

(56) References Cited

U.S. PATENT DOCUMENTS

| | | | |
|---|---|---|---|
| 6,312,612 B1 | 11/2001 | Sherman et al. | |
| 2009/0035446 A1 | 2/2009 | Kwon | |
| 2012/0027837 A1 | 2/2012 | DeMuth et al. | |
| 2014/0180201 A1 | 6/2014 | Ding et al. | |
| 2014/0207101 A1* | 7/2014 | Moeckly | A61M 37/0015 604/173 |

(Continued)

FOREIGN PATENT DOCUMENTS

| | | |
|---|---|---|
| KR | 10-2007-0102666 A | 10/2007 |
| KR | 10-2014-0147040 A | 12/2014 |

(Continued)

OTHER PUBLICATIONS

International Search Report; issued in PCT/KR2019/010876; mailed Dec. 4, 2019.

(Continued)

*Primary Examiner* — Dung T Ulsh
(74) *Attorney, Agent, or Firm* — Studebaker & Brackett PC

(57) ABSTRACT

The present invention relates to a perforated plate microstructure module, and more particularly, to a perforated plate microstructure module which can be used to deliver a drug into the skin.

19 Claims, 12 Drawing Sheets

(56) References Cited

U.S. PATENT DOCUMENTS

2015/0290444 A1* 10/2015 Wirtanen .......... A61M 37/0015
                                                                        604/46
2016/0361527 A1* 12/2016 Jung ................ A61M 37/0015
2017/0239457 A1* 8/2017 Asai ................. A61M 37/0015

FOREIGN PATENT DOCUMENTS

| KR | 10-1747099 B1 | 6/2017 |
| KR | 10-1816922 B1 | 1/2018 |
| KR | 10-1830398 B1 | 2/2018 |
| KR | 10-1853308 B1 | 4/2018 |

OTHER PUBLICATIONS

Written Opinion; issued in PCT/KR2019/010876; mailed Dec. 4, 2019.

* cited by examiner

PERFORATED PLATE MICROSTRUCTURE MODULE

CROSS-REFERENCE TO RELATED APPLICATIONS

The present application is a continuation of International Patent Application No. PCT/KR2019/010876, filed on Aug. 27, 2019, which is based upon and claims the benefit of priority to Korean Patent Application Nos. 10-2018-0101288 and 10-2018-0101293 filed with the Korean Intellectual Property Office on Aug. 28, 2018. The disclosures of the above-listed applications are hereby incorporated by reference herein in their entirety.

TECHNICAL FIELD

The present invention relates to a perforated plate microstructure module, and more particularly, to a perforated plate microstructure module which can be used to deliver a drug into the skin.

BACKGROUND ART

In general, tablets or capsules are orally administered or injection needles are used to deliver drugs for treatment of diseases or cosmetic products into a body. Recently, various microstructures including microneedles have been developed. The microstructures developed up to date have been mainly used to deliver a drug into a living body, collect blood, and detect analytes in the body.

A biodegradable microneedle in the related art is not dissolved immediately when the biodegradable microneedle is inserted into the skin, but the biodegradable microneedle is dissolved completely depending on the used substance, and it takes several minutes to several tens of minutes to dissolve the biodegradable microneedle. Therefore, a patch, which may be fixed to the skin, is used to prevent the microneedle from being separated from the skin while the microneedle is dissolved in the skin after being inserted into the skin.

However, in the process of inserting the microneedle using the patch, there are problems such as skin irritation caused by attachment and detachment of the patch, limitations in amount of loaded drug due to a small size of the microneedle, difficulty in delivering a drug in accurate quantity due to residues remaining on the patch after dissolution of the microneedle, a deterioration in insertion rate of the microneedle caused when human hair pushes the patch from the skin on which the human hair exists and the human hair interrupts adhesion between the patch and the skin, and difficulty in attaching the patch onto a curved portion of the skin, such as a wrinkle or a join, or a moving portion.

Meanwhile, in order to apply the microneedle to a shooting device for inserting the microneedle into the skin, the microneedles are manufactured on a biodegradable film, and only the biodegradable film on which the microneedles exist is separated and sized to be suitable for a perforated plate. The film having the adjusted size is placed and mounted on the perforated plate having openings corresponding to the microneedles, and a pillar is used to push the microneedles, thereby inserting the microneedles into the skin.

The shooting device in the related art may completely implant the microstructure into the skin, but the perforated layer is in contact with the skin when the microstructure is implanted, and the pillar is also inserted into the skin when the pillar pushes the microstructure. In particular, because the perforated layer and the pillar of the shooting device in the related art are integrally formed, it is difficult to replace the perforated layer and the pillar.

Therefore, when the shooting device is reused, the perforated layer and the pillar, which were in contact with the skin during previous use, come into contact with another subject's skin, which causes a hygienic problem such as secondary infection.

In order to solve the above-mentioned problem, there is an increasing need for a microstructure module capable of preventing a part, which is to be in contact with the skin, from being reused, and limiting the use of the part to a single use.

DETAILED DESCRIPTION OF THE INVENTION

Technical Problem

The present invention has been made in an effort to solve the above-mentioned problems in the related art, and an object of the present invention is to provide a perforated plate microstructure module which is easily replaced to limit use of a part, which is to be in contact with or inserted into skin, in a single use.

Another object of the present invention is to provide a perforated plate microstructure module capable of providing a constant administration amount of drug to be delivered into the skin and increasing the administration amount of drug.

Technical Solution

A perforated plate microstructure module according to the present invention includes: a perforated plate having one or more openings; base parts provided in the one or more openings; microneedles provided on the base parts; and a pressing member positioned to be spaced apart from the perforated plate and including one or more pillars provided to press the base parts, in which the base part and the perforated plate coupled are separable by force of 0.01 N to 100 N.

The base part and the microneedle may contain different compositions.

The base part and the microneedle may contain the same composition.

The opening may be convex inward.

The base part may fill a part or the entirety of an interior of the opening so that the microneedle is positioned on the base part.

The base part may be 1% to 100% of a height of the perforated plate.

The base part may contain hyaluronic acid.

The base part may contain triamcinolone.

The microneedle may contain a medicinally active ingredient.

The coupling force between the base part and the perforated plate may be adjusted by one or more of a material of the perforated plate, a material of the base part, a height of the base part, and plasma surface treatment.

The one or more pillars and the base part may be in contact with one another or spaced apart from one another at an interval of 1 cm or less.

The base part or the microneedle may contain a biodegradable substance.

The biodegradable or biocompatible substance may be polyester, polyhydroxyalkanoate (PHAs), poly(α-hydroxyacid), poly(β-hydroxyacid), poly(3-hydroxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(imino carbonate), poly(tyrosine carbonate), polycarbonate, poly(tyrosine arylate), polyalkylene oxalate, polyphosphazene, PHA-PEG, ethylene vinyl alcohol copolymer (EVOH), polyurethane, silicone, polyester, polyolefin, polyisobutylene and ethylene-alphaolefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoro alkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, or glycogen, and particularly, may contain one or more substances selected from polyester, polyhydroxyalkanoate (PHAs), poly(α-hydroxyacid), poly(β-hydroxyacid), poly(3-hydrosoxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyether ester, polyanhydride, poly(glycolic acid-co-trimethylene carbonate), polyphosphoester, polyphosphoester urethane, poly(amino acid), polycyano acrylate, poly(trimethylene carbonate), poly(imino carbonate), poly(tyrosine carbonate), polycarbonate, poly(tyrosine arylate), polyalkylene oxalate, polyphosphazene, PHA-PEG, chitosan, dextran, cellulose, heparin, hyaluronic acid, alginate, inulin, starch, and glycogen.

The perforated plate or the base part may be made of a hydrophilic material.

Advantageous Effects

According to the perforated plate microstructure module according to the exemplary embodiment of the present invention, the perforated layer and the pillar, which are to be in contact with or inserted into the skin, are provided in the integrated module, such that the perforated plate microstructure module may be replaced and discarded after single use, thereby preventing a hygienic problem such as secondary infection.

The perforated plate microstructure module according to the exemplary embodiment of the present invention may implant the microstructure without an adhesive sheet, such that the perforated plate microstructure module may be used for a curved or frequently moving joint area, thereby minimizing the restriction of the implantation site.

According to the shooting microstructure module according to another exemplary embodiment of the present invention, the microstructure is completely implanted in the skin, such that an accurate amount of drug may be delivered, thereby improving an efficacy of delivering the drug and safety and uniformity in using the drug.

EXPLANATION OF REFERENCE NUMERALS AND SYMBOLS

Figure 1:
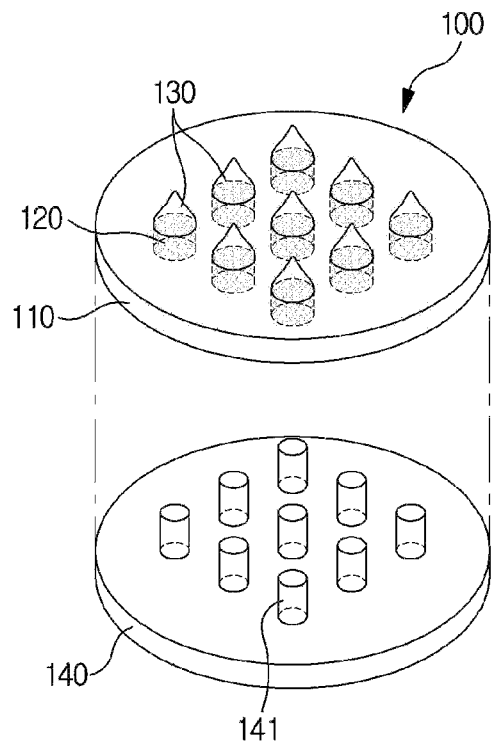
FIG. 1 is a view illustrating a configuration of a perforated plate microstructure module according to an exemplary embodiment of the present invention.

100: Perforated plate microstructure module
110: Perforated plate
111: Opening
120: Base part
130: Microneedle
140: Pressing member
141: Pillar
20: Applicator
21: Main body housing 22: Pushing member
23: Piston
24: Screw thread
200: Shooting microstructure module
210: Housing
220: Perforated layer
222: Opening
224: Support part
230: Shooting microstructure
232: Base part
234: Microneedle
240: Pressing member
241, 242: Plate
244: Pillar
246: Catching part
248: Through port
251, 252, 253: Coupling member
261,262: Groove portion
263: Push button
1: Module frame
2: Skin
3: Shooting member

BEST MODE

The detailed description of the present invention is provided to completely explain the present invention to a person with ordinary skill in the art. Throughout the specification, unless explicitly described to the contrary, when one component "comprises (includes)" another component or "characterized by" having a certain structure and a certain shape, this means that other components, structures, and shapes may be included without being excluded.

The present invention may be variously modified and may have various exemplary embodiments, and specific exemplary embodiments will be described in detail in the detailed description. However, the description of the exemplary embodiments is not intended to limit the contents of the present invention, but it should be understood that the present invention is to cover all modifications, equivalents and alternatives falling within the spirit and technical scope of the present invention.

FIG. 1 is a view illustrating a configuration of a perforated plate microstructure module 100 according to an exemplary embodiment of the present invention. Referring to FIG. 1, the perforated plate microstructure module 100 according to the exemplary embodiment of the present invention includes a perforated plate 110, base parts 120, microneedles 130, and a pressing member 140.

The perforated plate microstructure module 100 may be configured such that the pressing member 140 having one or more pillars 141 is disposed at a side of the perforated plate 110 at which no microneedle 130 is formed.

The pressing member 140 having one or more pillars 141 may be in contact with the perforated plate 110 including the base parts 120 or spaced apart from the perforated plate 110 at an interval of 1 cm or less.

Figure 2:
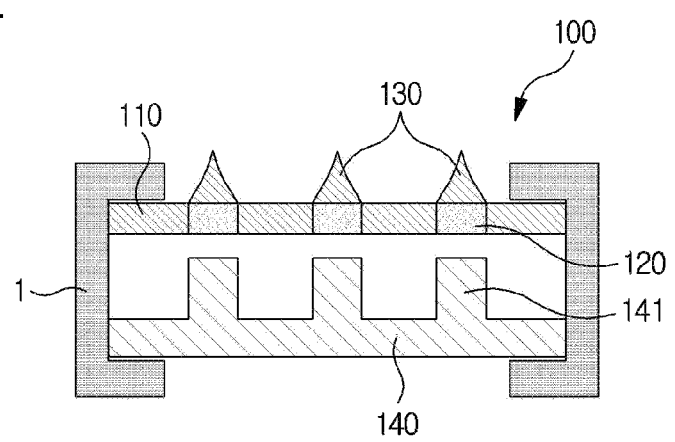
FIG. 2 is a cross-sectional view illustrating the perforated plate microstructure module according to the exemplary embodiment of the present invention.

FIG. 2 is a cross-sectional view of the perforated plate microstructure module 100. Referring to FIG. 2, the perforated plate microstructure module 100 may be configured such that the perforated plate 110 and the pressing member 140 are coupled to a module frame 1. All the components of the perforated plate microstructure module 100 may be integrated and used for a single use.

The perforated plate 110 functions to include a drug delivery medium with low coupling force so that the drug delivery medium is easily delivered to the user's skin. In order to perform this function, one or more openings 111, which are spaced apart from one another at predetermined intervals, are formed in a central portion of the perforated plate 110, and a part or the entirety of each of the openings 111 may be filled with the base part 120 to be described below.

The perforated plate 110 may have strength enough to prevent the perforated plate 110 from being deformed or broken by physical force when the physical force for inserting the microneedles 130 into the skin is applied. The perforated plate 110 is coupled to the base part 120 with low coupling force so that the microneedle 130 may be easily separated when the external physical force is applied.

The external physical force may be 0.01 to 100 N. When the physical force is lower than 0.01 N, the base part 120 cannot be easily separated from the perforated plate 110. In contrast, when the physical force is higher than 100 N, the force applied to the skin by the microneedle 130 increases, which causes pain in the skin. The external physical force, which is applied to insert the microneedles 130 into the skin, may be adjusted by the number of openings 111 included in the perforated plate 110.

The opening 112 may be convex inward or a coating layer is additionally provided between the base part 120 and the perforated plate 110 in order to compensate for the low coupling force and prevent the perforated plate 110 and the base part 120 from being separated from each other during storage and transport due to the low coupling force.

The perforated plate 110 and the base part 120 to be described below may be made of a hydrophilic material. For example, the hydrophilic material may include a hydrophilic polymer including, as a monomer, hyaluronic acid (HA), carboxymethyl cellulose (CMC), methacrylic acid (MA), 2-hydroxyethyl methacrylate (HEMA), ethyl acrylate (EA), 1-vinyl-2-pyrrolidinone (VP), propenoic acid 2-methyl ester (PAM), monomethacryloyloxyethyl phthalate (EMP), or ammonium sulphatoethyl methacrylate (SEM).

The base parts 120 may be formed in the one or more openings 111 formed in the perforated plate 110 and may function to support the microneedles 130 to be described below. In order to perform this function, the base part 120 may fill a part or the entirety of the opening 111 of the perforated plate 110.

Specifically, the base part 120 may occupy 1% to 100% of a height of the perforated plate 110. If the base part 120 occupies less than 1% of the height of the perforated plate 110, the microneedle 130 and the base part 120 may be separated from the perforated plate 110 during a process of changing a shape after spotting a viscous composition on the base part 120.

The base part 120 is configured to be inserted into the skin together with the microneedle 130 to be described below, and the base part 120 may be made of a biodegradable substance or may include a drug. Therefore, the base part 120 may contain the same composition as the microneedle 130 containing the drug, or the base part 120 and the microneedle 130 may have different compositions.

In addition, the coupling force between the base part 120 and the perforated plate 110 may be lower than physical force applied to shoot the microneedle 130. The coupling force between the base part 120 and the perforated plate 110 may be adjusted depending on one or more of a material of the perforated plate 110, a material of the base part 120, a height of the base part 120, and plasma surface treatment.

In this case, the material of the perforated plate 110 and the material of the base part 120 may vary depending on the type and concentration of the material constituting the perforated plate 110 and the base part 120.

In order to adjust the coupling force between the base part 120 and the perforated plate 110, the perforated plate 110 may be made of any one of plastic such as polycarbonate (PC), general purpose polystyrene (GPPS), and polymethyl methacrylate (PMMA), metal, and a ductile material such as rubber.

The surface treatment on the perforated plate 110 may include chemical treatment, ultraviolet irradiation, and plasma treatment. Specifically, the coupling force between the base part 120 and the perforated plate 110 may be adjusted in accordance with the type and concentration of chemical substances used for the chemical treatment, and intensity and time of emission of the ultraviolet rays and the plasma.

The microneedle 130 may be separated from the perforated plate 110 by the pressing member 140 to be described below to function to deliver the drug into the user's skin. In order to perform this function, the microneedle 130 may be provided on the base part 120 and made of a biocompatible or biodegradable substance including a drug.

The microneedle 130 may be formed by spotting a viscous composition containing a biocompatible or biodegradable substance on the base part 120. In this case, the term "viscous composition" means a composition having an ability to form the microneedle by changing in shape.

The microneedle 130 may have a circular horizontal cross section. In this case, a portion of the microneedle 130, which is to be joined to the base part 120, may have a circular shape having a predetermined area.

In the present specification, the term "biocompatible substance" means a substance which is substantially not toxic to a human body, is chemically inactive, and is not immunogenic. In the present specification, the term "biodegradable substance" means a substance that may be degraded by a bodily fluid, a microorganism, or the like in a living body.

For example, the biocompatible or biodegradable substance, which may be used in the present invention, may be polyester, polyhydroxyalkanoate (PHAs), poly($\alpha$-hydroxyacid), poly($\beta$-hydroxyacid), poly(3-hydroxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyetherester, polyanhydride, poly(glycolic acid-co-trimethylene carbonate), polyphosphoester, polyphosphoester urethane, poly(amino acid), polycyanoacrylate, poly(trimethylene carbonate), poly(imino carbonate), poly(tyrosine carbonate), polycarbonate, poly(tyrosine arylate), polyalkylene oxalate, polyphosphazene, PHA-PEG, ethylene vinyl alcohol copolymer (EVOH), polyurethane, silicone, polyester, polyolefin, polyisobutylene and ethylene-alphaolefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoro alkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, or glycogen, and particularly, may contain one or more substances selected from polyester, polyhydroxyalkanoate (PHAs), poly($\alpha$-hydroxyacid), poly($\beta$-hydroxyacid), poly(3-hydroxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyether ester, polyanhydride, poly(glycolic acid-co-trimethylene carbonate), polyphosphoester, polyphosphoester urethane, poly(amino acid), polycyano acrylate, poly(trimethylene carbonate), poly(imino carbonate), poly(tyrosine carbonate), polycarbonate, poly(tyrosine arylate), polyalkylene oxalate, polyphosphazene, PHA-PEG, chitosan, dextran, cellulose, heparin, hyaluronic acid, alginate, inulin, starch, and glycogen.

In the present invention, the drug, which may be used for the microneedle 130, is not particularly limited. For example, the drug includes a chemical drug, a protein drug, a peptide drug, nucleic acid molecules for gene therapy, nanoparticles, functional cosmetic effective ingredients, and cosmetic ingredients.

For example, the drug, which may be used in the present invention, includes, but not limited to, an anti-inflammatory drug, an analgesic, an anti-arthritis drug, an antispasmodic, an antidepressant, an antipsychotic drug, a tranquilizer, an anti-anxiety drug, a drug antagonist, an anti-parkinsonism drug, a cholinergic agonist, an anticancer drug, an antiangiogenic drug, an immunosuppressant, an antiviral drug, an antibiotic, an appetite suppressant, an analgesic, an anticholinergic, an antihistamine, an antimigraine drug, hormones, a coronary vasodilator, a cerebral vasodilator, a peripheral vasodilator, a contraceptive, an antithrombotic drug, a diuretic, an antihypertensive agent, a therapeutic agent for cardiovascular disease, and a cosmetic ingredient (e.g., an anti-wrinkle agent, a skin aging inhibitor, and a skin whitening agent).

While the perforated plate microstructure module 100 according to the exemplary embodiment of the present invention has been described as including the plurality of microneedles 130, the number of microneedles 130 is not particularly limited as long as the perforated plate microstructure module 100 may perform the above-mentioned functions. For example, the perforated plate microstructure module 100 according to the present invention may include the single microneedle 130 using a highly concentrated formulation.

The pressing member 140 may function to separate the base part 120 and the microneedle 130 from the perforated plate 110 by using the physical force applied from the outside. In order to perform this function, the pressing member 140 includes the one or more pillars 141 and may have strength enough to prevent the pressing member 140 from being deformed or damaged by the physical force when the physical force is applied.

Figure 3:
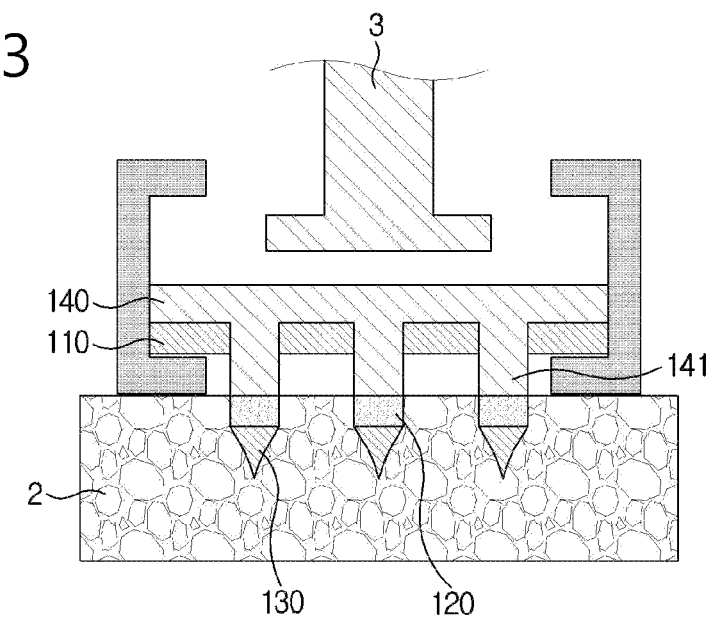
FIG. 3 is a cross-sectional view illustrating a state in which microneedles are inserted into skin by a pressing member according to the exemplary embodiment of the present invention.

FIG. 3 is a cross-sectional view illustrating a state in which the microneedles 130 are inserted into the skin by the pressing member 140 according to the exemplary embodiment of the present invention.

Referring to FIG. 3, the one or more pillars 141 are provided on the pressing member 140 so as to correspond to the positions of the openings 111 of the perforated plate 110, such that the pressing member 140 may separate the base part 120 from the perforated plate 110 by using the force applied from the outside.

Specifically, the physical force applied to the pillar 141 may push downward the base part 120, which is formed in the opening 111, from the perforated plate 110 to insert the base part 120 into the skin 2 by a predetermined depth. Because the physical force applied to the pillar 141 is higher than the coupling force between the base part 120 and the perforated plate 110, the base part 120 may be easily separated from the perforated plate 110 by the pressing force of the pillar 11.

Figure 4:
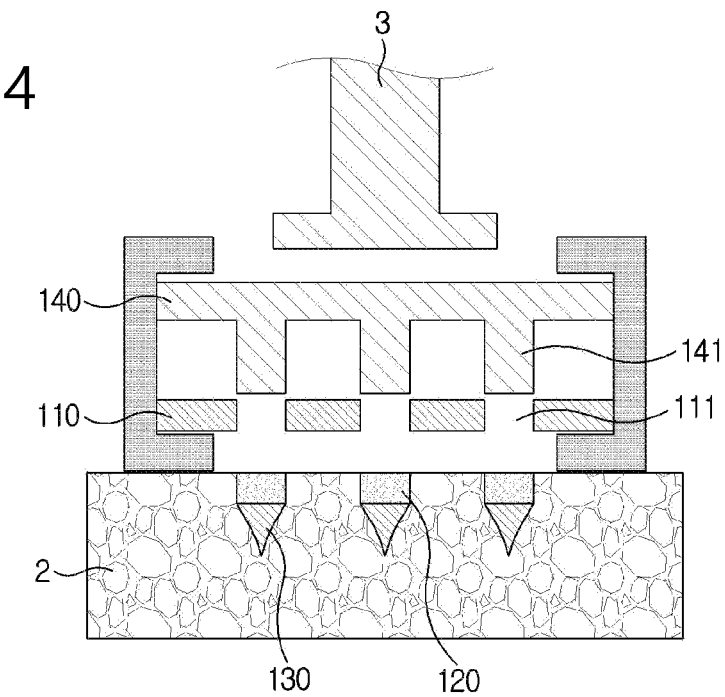
FIG. 4 is a cross-sectional view illustrating a state in which the perforated plate microstructure module according to the exemplary embodiment of the present invention is returned back to an original state after the microneedles are inserted into the skin.

FIG. 4 is a cross-sectional view illustrating a state in which the perforated plate microstructure module 100 is returned back to an original state after the microneedle 130 is inserted into the skin.

Referring to FIG. 4, it can be seen that when the base part 120 is separated from the perforated plate 110 by the pressing member 140, the base part 120 is inserted into the skin 2 in a state in which the base part 120 is coupled to the microneedle 130 without being separated from the microneedle 130, and only the vacant opening 111 exists in the perforated plate 110.

Meanwhile, the exemplary embodiment of the present invention provides a shooting member 3 for providing the force applied from the outside, but it should be noted that a method of applying the physical force is not limited to a particular method and may be configured as methods using hydraulic pressure, pneumatic pressure, and an elastic body.

Figure 5:
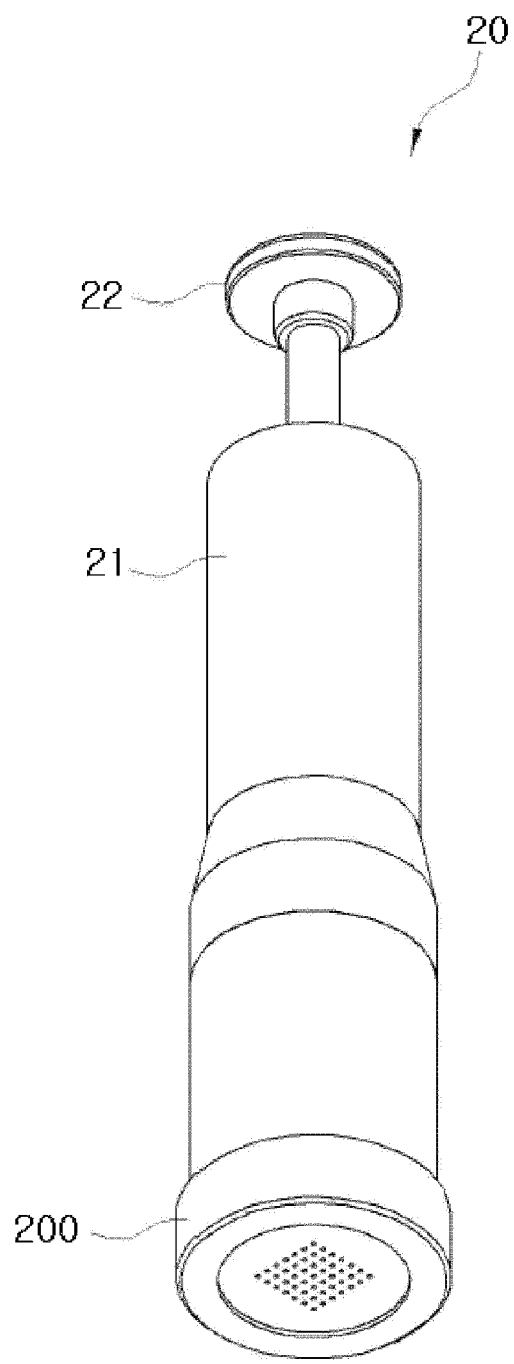
FIG. 5 is a perspective view illustrating a state in which a shooting microstructure module according to another exemplary embodiment of the present invention is mounted on an applicator.
Figure 6:
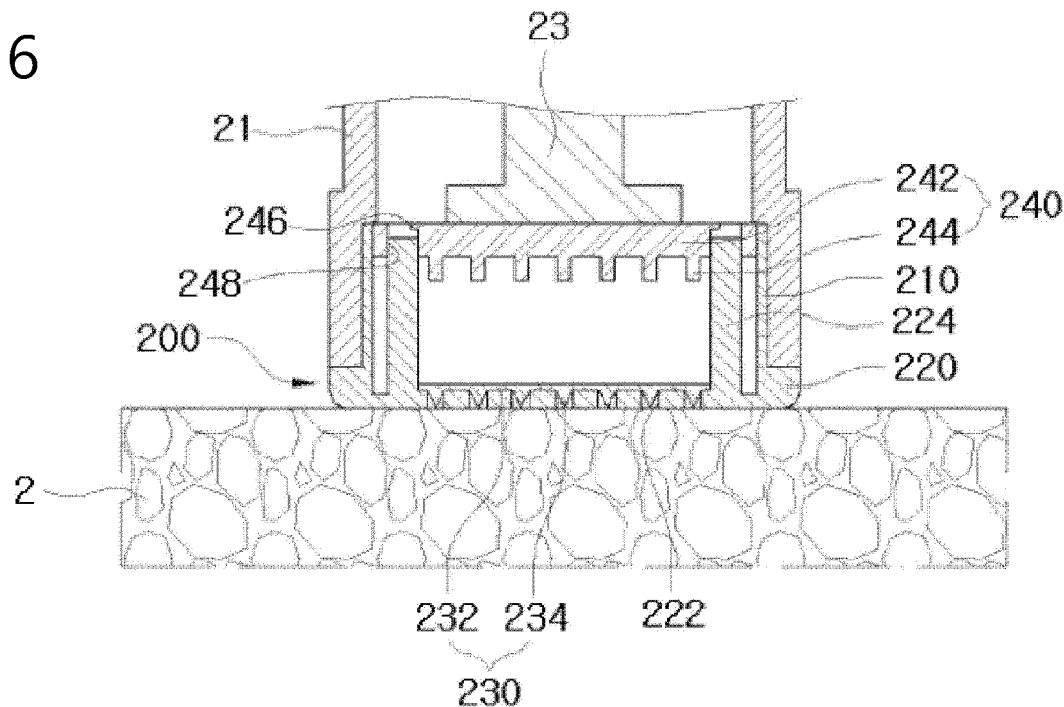
FIG. 6 is a cross-sectional view illustrating the shooting microstructure module side illustrated in FIG. 5.

Hereinafter, a shooting microstructure module and an applicator according to another exemplary embodiment of the present invention will be described in detail with reference to the drawings. FIG. 5 is a perspective view illustrating a state in which the shooting microstructure module according to another exemplary embodiment of the present invention is mounted on the applicator, and FIG. 6 is a cross-sectional view illustrating the shooting microstructure module side illustrated in FIG. 5.

Referring to FIG. 5, a shooting microstructure module 200 is detachably mounted on an applicator 20 according to another exemplary embodiment of the present invention. In this case, the shooting microstructure module 200 may function as a head of the applicator 20.

According to the present invention, a perforated layer, which is to be in contact with the skin, and a pillar, which is to be inserted into the skin, may be separately configured in the shooting microstructure module 200 and configured to be attachable to and detachable from the applicator 20, such that the pillar and the perforated layer may be easily replaced after single use, thereby preventing a risk of secondary infection during the process of implanting the microstructure.

The applicator 20 serves to implant the microstructure mounted on the shooting microstructure module 200 into the skin and includes a main body housing 21 and shooting members 12 and 13.

The main body housing 21 has a cylindrical shape, but the present invention is not particularly limited to the shape of the main body housing 21. A through port (not illustrated) for a pushing member 22 is positioned at an upper side of the main body housing 21, and the shooting microstructure module 200 is mounted at a lower side of the main body housing 21.

The shooting members 12 and 13 are provided in the main body housing 21 to press the pressing member or the microstructure of the shooting microstructure module 200, and the shooting members 12 and 13 include a pushing member 22 and a piston 23.

The pushing member 22 protrudes outward through the through port (not illustrated) provided at one side of the main body housing 21. The pushing member 22 is manipulated by a user to shoot the piston 23 toward a pressing member 240 of the shooting microstructure module 200. In this case, the term "shooting" means that the microneedle 234 moves forward and is separated from the shooting microstructure module 200.

Referring to FIG. 6, the piston 23 may press the pressing member 240 of the shooting microstructure module 200 by the manipulation of the pushing member 22. In this case, for simplification of the drawings, an elastic member received in the main body housing 21 and configured to provide pressing force to the piston 23 is omitted and constituent elements associated with the elastic member are omitted.

The example in which the pushing member 22 and the piston 23 are provided as the shooting members has been described, but the present invention is not particularly limited thereto. That is, the shooting member is not particularly limited as long as the shooting member presses pillars 244 of the shooting microstructure module 200.

Because the microneedle 234 may be implanted in the skin 2 by the applicator 20 without an adhesive sheet, the microneedle 234 may be used for a curved or frequently moving joint area, thereby minimizing the restriction of the implantation site, like a micro-patch.

The shooting microstructure module 200 includes a housing 210, a perforated layer 220, a shooting microstructure 230, and the pressing member 240.

An upper side of the housing 210 is attachable to and detachable from the applicator 20, and the housing 210 has a hollow portion. The housing 210 may have a cylindrical shape, but the present invention is not particularly limited thereto. The housing 210 has a coupling member to be coupled to the applicator 20, and the coupling member will be described below with reference to FIGS. 12 to 14.

The perforated layer 220 is provided at a lower side of the housing 210 and has one or more openings 222. In this case, the perforated layer 220 may be formed integrally with the housing 210. In this case, the housing 210 may define a sidewall of the perforated layer 220.

Figure 7:
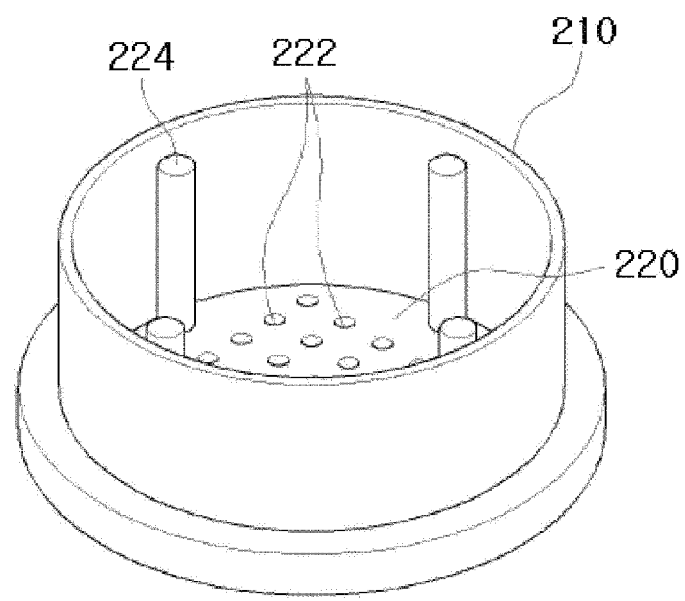
FIG. 7 is a perspective view illustrating a housing and a perforated layer illustrated in FIG. 6.

FIG. 7 is a perspective view illustrating the housing and the perforated layer illustrated in FIG. 6.

The perforated layer 220 may have support parts 224 for supporting the pressing member 240. In this case, the support parts 224 may be formed at the periphery of the one or more openings 222 so as not to constrain the shooting operation of the pillar 244.

As illustrated in FIG. 6, catching parts 246 provided on the pressing member 240 may be seated on the support parts 224. As a result, the support parts 224 may support the pressing member 240 so that the pillar 244 is disposed at a predetermined height from the perforated layer 220.

The shooting microstructure 230 includes base parts 232 and microneedles 234. In this case, the shooting microstructure 230 is disposed in the housing 210 and mounted on an upper portion of the perforated layer 220.

The base part 232 has a plate shape, and the one or more microneedles 234 are provided on surfaces of the base parts 232. In this case, the one or more microneedles 234 are provided on the surfaces of the base parts 232 and disposed at positions corresponding to the openings 222 of the perforated layer 220.

In the present invention, the drug, which may be used for the microneedle 234, is not particularly limited. For example, the drug includes a chemical drug, a protein drug, a peptide drug, nucleic acid molecules for gene therapy, nanoparticles, functional cosmetic effective ingredients, and cosmetic ingredients.

For example, the drug, which may be used in the present invention, includes, but not limited to, an anti-inflammatory drug, an analgesic, an anti-arthritis drug, an antispasmodic, an antidepressant, an antipsychotic drug, a tranquilizer, an anti-anxiety drug, a drug antagonist, an anti-parkinsonism drug, a cholinergic agonist, an anticancer drug, an antiangiogenic drug, an immunosuppressant, an antiviral drug, an antibiotic, an appetite suppressant, an analgesic, an anticholinergic, an antihistamine, an antimigraine drug, hormones, a coronary vasodilator, a cerebral vasodilator, a peripheral vasodilator, a contraceptive, an antithrombotic drug, a diuretic, an antihypertensive agent, a therapeutic agent for cardiovascular disease, and a cosmetic ingredient (e.g., an anti-wrinkle agent, a skin aging inhibitor, and a skin whitening agent).

In addition, in the present invention, the material of the microneedle 234 contains a biocompatible or biodegradable substance. In the present specification, the term "biocompatible substance" means a substance which is substantially not toxic to a human body, is chemically inactive, and is not immunogenic. In the present specification, the term "biodegradable substance" means a substance that may be degraded by a bodily fluid, a microorganism, or the like in a living body.

In this case, the microneedle 234 may be formed by spotting viscous compositions of drugs. In this case, the term "viscous composition" means a composition having an ability to form the microstructure by changing in shape.

The microneedle 234 has a circular horizontal cross section. In this case, a portion of the microneedle 234, which is to be joined to the base part 232, has a circular shape having a predetermined area. The microneedle 234 may include a pointed end portion at a portion of the microneedle 234 which is to be implanted in the skin 2.

In this case, the microneedle 234 may be disposed in the housing 210 so that the end portion of the microneedle 234 does not protrude outward from the opening 222 in order to protect the end portion thereof. For example, a height of the microneedle 234, from the base part 232 to the end portion, may be smaller than a depth of the opening 222.

Figure 8:
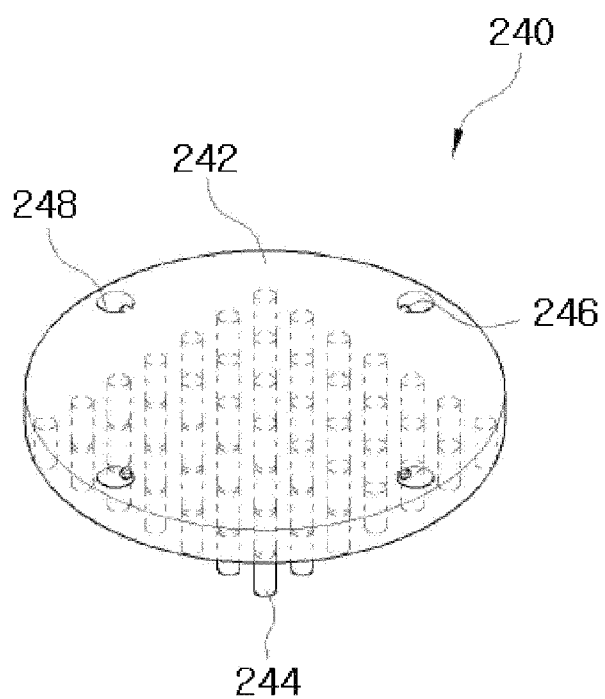
FIG. 8 is a perspective view illustrating the pressing member illustrated in FIG. 6.

The pressing member 240 includes a plate 242, the pillars 244, and the catching parts 246. FIG. 8 is a perspective view illustrating the pressing member illustrated in FIG. 6.

The plate 242 may have a plate shape corresponding to a cross-sectional shape of the housing 210 so that the plate 242 may be received in the housing 210. FIG. 8 illustrates that the plate 242 has a circular shape, but the present invention is not particularly limited thereto.

The pillars 244 may be provided on one surface of the plate 242. For example, the one or more pillars 244 may be provided on a lower surface of the plate 242 and disposed at the positions corresponding to the microneedles 234 and the openings 222. In this case, the pillars 244 may have the same length.

The lengths of the pillars 244 may vary depending on the positions on the plate 242 at which the pillars 244 are provided. For example, the pillars 244, which are provided at an outer peripheral portion and a central portion of the plate 242, may have different lengths. In this case, the pillar provided at the outer peripheral portion of the plate may have a longer length than the pillar provided at the central portion of the plate.

As a result, in a case in which a distance between the plate 242 and the skin 2 varies depending on the shape of the curved skin 2, the microneedles 234 may be uniformly inserted into the curved skin 2 when the microneedles 234 are inserted into the curved skin 2 because the lengths of the pillars 244 vary depending on the shape of the curved skin 2.

In addition, the pillar 244 may have a length larger than a thickness of the opening 222 of the perforated layer 220. That is, the pillar 244 may protrude outward from the opening 222 in order to implant the microneedle 234 into the skin 2. In this case, the pillar 244, together with the microneedle 234, may be inserted into the skin 2.

The catching parts 246 may be provided at the positions corresponding to the support parts 224 of the perforated layer 220. In this case, the catching part 246 may be positioned at one end of the support part 224. As a result, the plate 242 may be disposed at a predetermined height from the perforated layer 220.

The catching part 246 may be formed to be broken by the shooting operations of the piston 23 and the pillar 244. That is, the catching part 246 may be broken by the pressing force applied to the plate 242.

For example, the catching part 246 may have a shape and a size corresponding to a cross section of the support part 224. In this case, the catching part 246 may be thinner than a thickness of the plate 242 so that the catching part 246 may be easily broken by the pressing force applied to the plate 242.

As another example, the plate 242 may have a through port 248 corresponding to a cross section of the support part 224, and the catching part 246 may be provided in at least a part of the through port 248. In this case, the catching part 246 may be thinner than a thickness of the plate 242 so that the catching part 246 may be easily broken by the pressing force applied to the plate 242.

As illustrated in FIG. 6, in the state in which the shooting microstructure module 200 is mounted on the applicator 20, the shooting microstructure module 200 brings the microneedles 234 into close contact with the skin 2 in order to implant the microneedles 234 into the skin 2.

In this case, as the support parts 224 of the perforated layer 220 are caught by the catching parts 246 of the plate 242, the pressing member 240 may be disposed at the predetermined height from the perforated layer 220. In this case, the shooting microstructure 230 may remain mounted on the upper portion of the perforated layer 220.

Hereinafter, the operation of the applicator 20 implanting the microneedles 234 into the skin 2 will be described in detail with reference to FIGS. 9 to 11.

Figure 9:
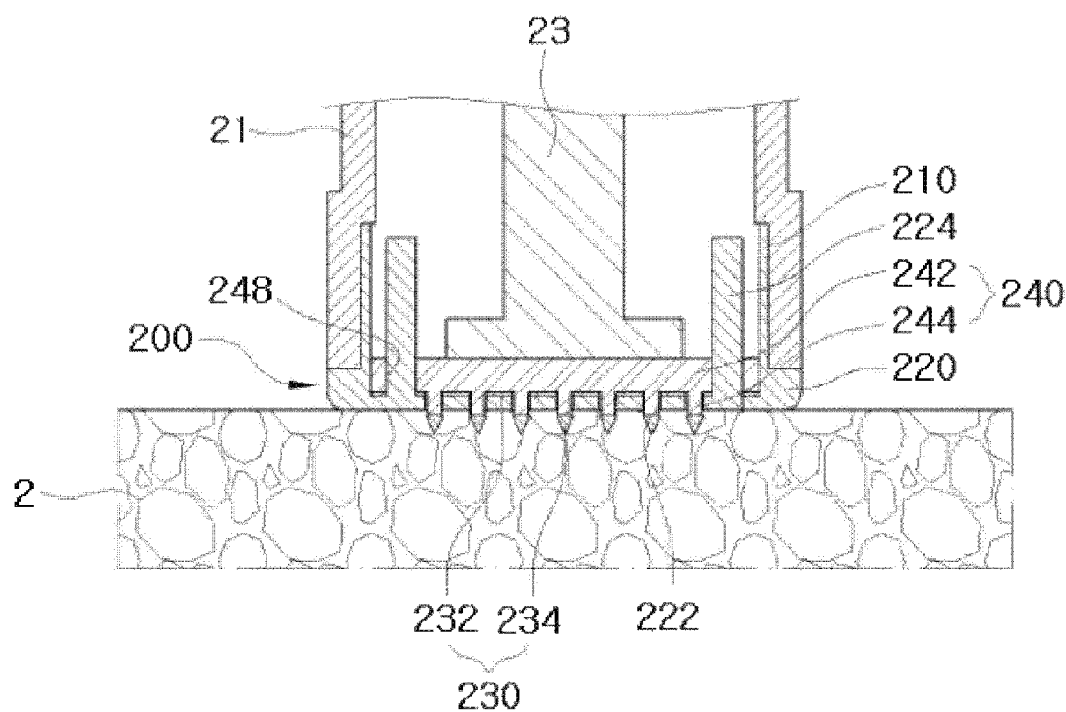
FIG. 9 is a cross-sectional view illustrating a state in which the applicator illustrated in FIG. 6 performs shooting.
Figure 10:
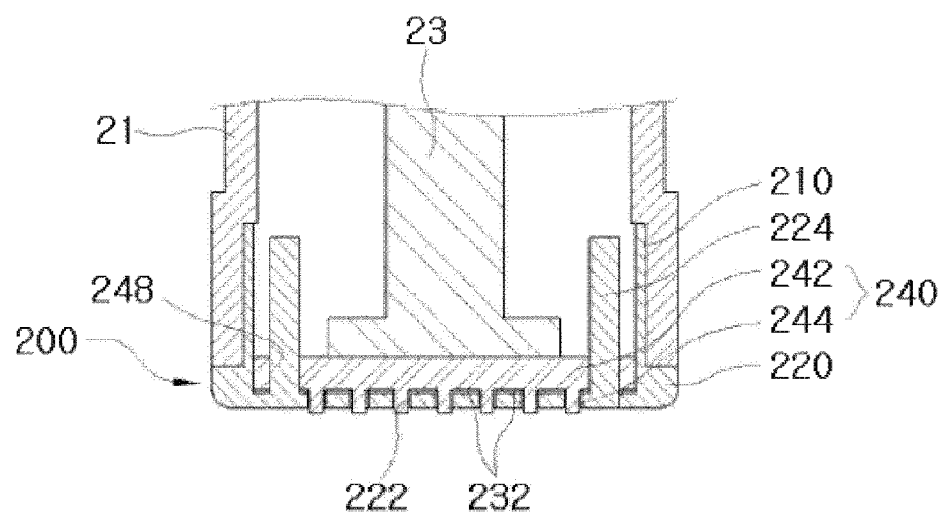
FIG. 10 is a cross-sectional view illustrating a state in which the microneedles illustrated in FIG. 9 are separated.
Figure 10:
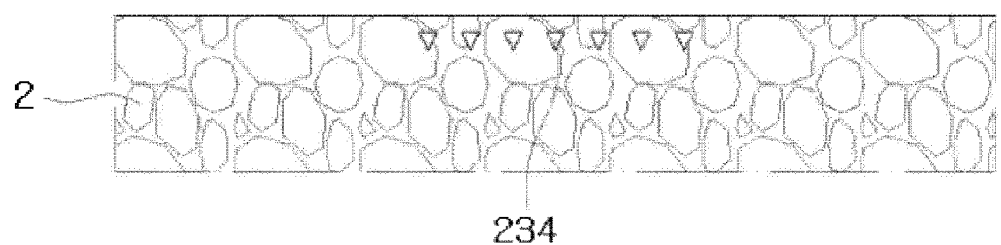
Figure 11:
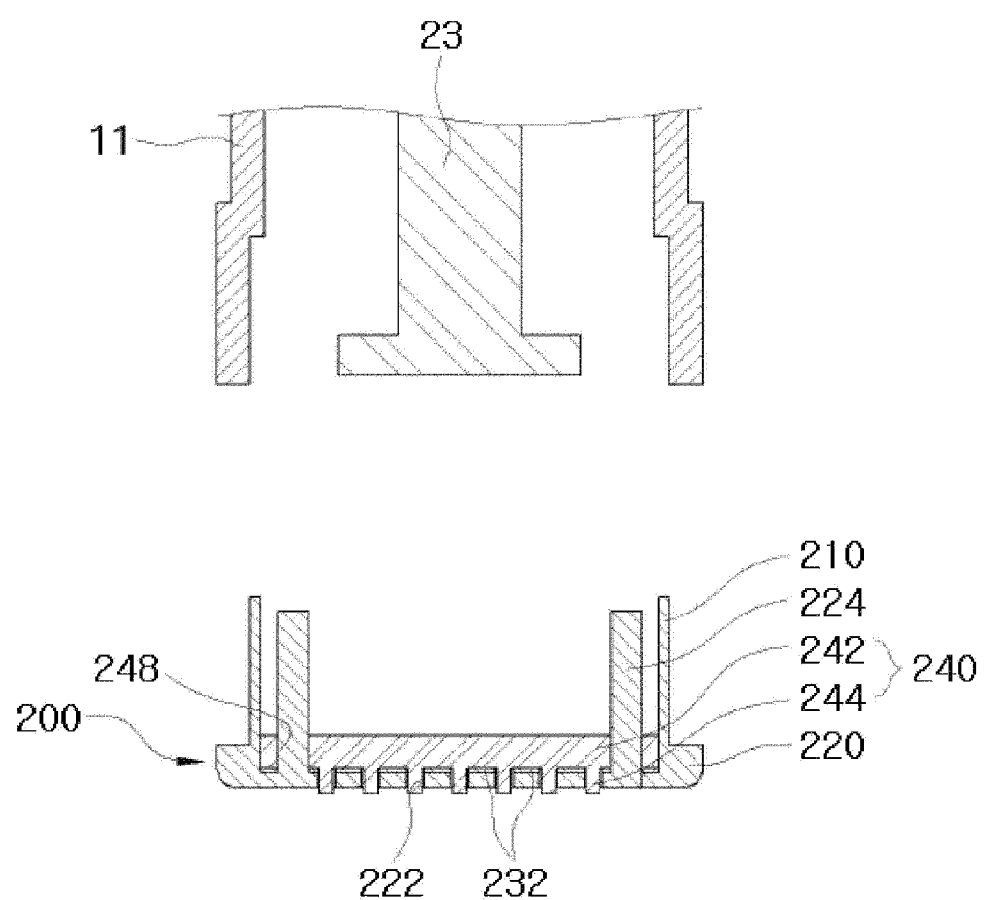
FIG. 11 is a cross-sectional view illustrating a state in which the microstructure module illustrated in FIG. 10 is separated from the applicator.

FIG. 9 is a cross-sectional view illustrating a state in which the applicator illustrated in FIG. 6 performs shooting, FIG. 10 is a cross-sectional view illustrating a state in which the microstructure illustrated in FIG. 9 is separated, and FIG. 11 is a cross-sectional view illustrating a state in which the shooting microstructure module illustrated in FIG. 10 is separated from the applicator.

Referring to FIG. 6, when the user shoots the applicator 20 by using the pushing member 22, the piston 23 presses the plate 242. In this case, when the plate 242 is moved to the perforated layer 220 by the pressing force applied to the plate 242 by the piston 23, the catching part 246 is broken by the support part 224.

Referring to FIG. 9, as the catching part 246 is broken, the through port 248 of the plate 242 is guided to the support part 224. In this case, the constraint of the plate 242 by the restrictive force of the support part 224 is released, such that the plate 242 is shot to the perforated layer 220.

When the plate 242 is pressed to the perforated layer 220, the pillars 244 protrude outward through the openings 222 of the perforated layer 220. In this case, the pillars 244 penetrate an underlying layer of the shooting microstructure 230, such that the microneedles 234 may be separated from the base parts 232 and implanted into the skin 2.

Since the microneedles 234 are completely implanted into the skin 2, it is possible to improve the efficacy of delivering the drug through the microneedles 234. Since the accurate amount of drug contained in the microneedle 234 may be delivered, it is possible to improve stability and uniformity in using the drug.

Referring to FIG. 10, the applicator 20 is separated from the skin 2 in the state in which the microneedle 234 is implanted into the skin 2. In this case, in the state in which the microneedle 234 is implanted into the skin 2, the pillar 244 may be separated from the skin 2.

In this case, because the perforated layer 220 is in contact with the skin 2 and the pillar 244 is inserted into the skin 2, there is a high risk of secondary contamination in case of reuse. The shooting microstructure module 200 is replaced and discarded after single use, which prevents secondary contamination.

Referring to FIG. 11, in the state in which the piston 23 is retracted rearward by the pushing member 22 of the applicator 20, the shooting microstructure module 200 is separated from the applicator 20.

As described above, the shooting microstructure module 200 separated from the applicator 20 may be discarded. That is, since the perforated layer 220, which has been in contact with the skin 2, and the pillar 244, which has been inserted into the skin 2, are discarded, it is possible to prevent secondary contamination caused by reuse.

As illustrated in FIG. 6, a new shooting microstructure module 200 may be mounted on a lower side of the applicator 20.

Meanwhile, the shooting microstructure module 200 according to another exemplary embodiment of the present invention may further include a coupling member 251, 252, or 253 provided to couple the housing 210 to the applicator 20.

The coupling member 251, 252, or 253 may be configured by any one of rotation coupling, hook coupling, insertion coupling, catching coupling, magnetic coupling, and Velcro. In this case, the coupling method is not particularly limited to the above-mentioned coupling methods, and the shooting microstructure module 200 and the applicator 20 may be coupled in various ways. In this case, a coupling member, which corresponds to the coupling member 251, 252, or 253 formed on the housing 210, may be formed on the main body housing 21.

Since the coupling members facilitates the replacement of the perforated layer 220, which has been in contact with the skin 2, and the pillar 244, which has been inserted into the skin 2, it is possible to improve convenience of use and prevent a risk of secondary contamination caused by reuse.

Figure 12:
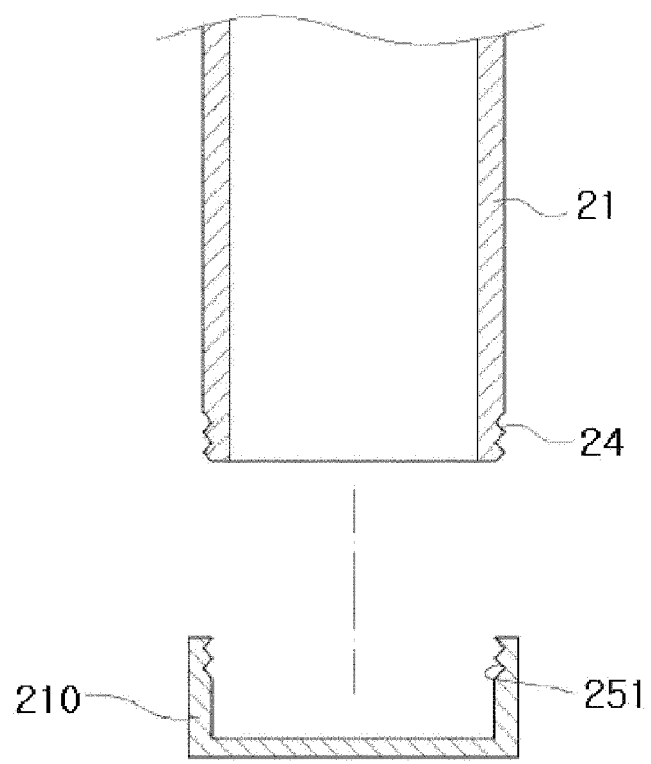
FIG. 12 is a cross-sectional view illustrating an example in which the shooting microstructure module according to another exemplary embodiment of the present invention is coupled to the applicator.

FIG. 12 is a cross-sectional view illustrating an example in which the shooting microstructure module according to the exemplary embodiment of the present invention is coupled to the applicator. In this case, for simplification of the drawings, the main body housing 21 of the applicator 20 and the housing 210 of the shooting microstructure module 200 are schematically illustrated.

Referring to FIG. 12, the shooting microstructure module 200 and the applicator 20 may be coupled by rotation coupling. In this case, a screw thread 24 may be formed along an outer circumference at one side of the main body housing 21, and the coupling member 251 may include a screw thread 24 formed along an inner circumference at one side of the housing 210.

Similarly, a screw thread 24 may be formed along an inner circumference at one side of the main body housing 21, and the coupling member 251 may include a screw thread 24 formed along an outer circumference at one side of the housing 210.

In this case, when the housing 210 is rotated in one direction below the main body housing 21, the screw thread 24 of the housing 210 is rotated along the screw thread 24 of the main body housing 21, and the housing 210 is moved to the main body housing 21, such that the housing 210 may be coupled to the main body housing 21, and as a result, the shooting microstructure module 200 may be coupled to the applicator 20.

On the contrary, when the housing 210 is rotated in a reverse direction in the state in which the shooting microstructure module 200 is coupled to the applicator 20, the screw thread of the housing 210 is rotated along the screw thread 24 of the main body housing 21, and the housing 210 is moved outward from the main body housing 21, such that the housing 210 may be separated from the main body housing 21, and as a result, the shooting microstructure module 200 may be separated from the applicator 20.

Figure 13:
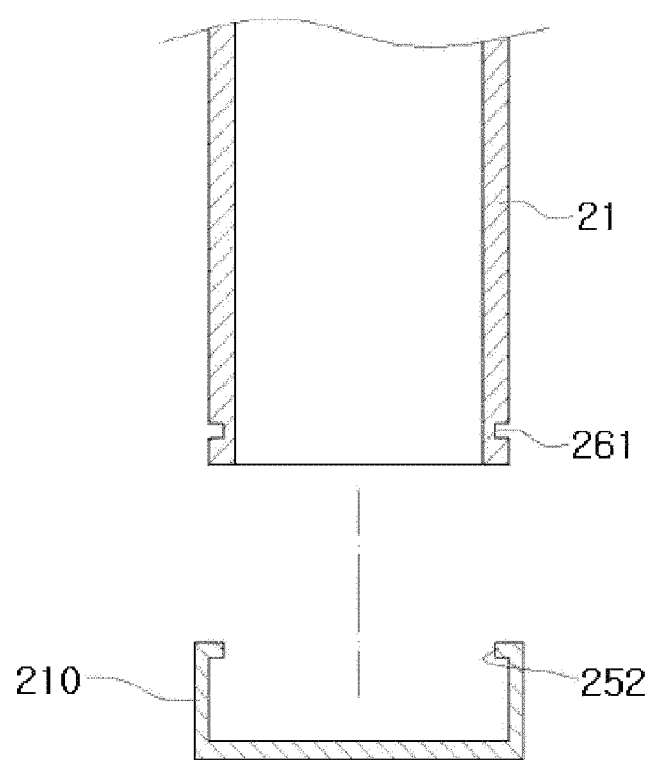
FIG. 13 is a cross-sectional view illustrating another example in which the shooting microstructure module according to another exemplary embodiment of the present invention is coupled to the applicator.

FIG. 13 is a cross-sectional view illustrating another example in which the shooting microstructure module according to the exemplary embodiment of the present invention is coupled to the applicator.

Referring to FIG. 13, the shooting microstructure module 200 and the applicator 20 may be coupled by catching coupling. In this case, a groove portion 261 is formed on an outer circumferential surface at one side of the main body housing 21, and the coupling member may include a protrusion portion 252 formed at one end of the housing 210 so as to correspond to the groove portion 261. The protrusion portion 252 may have elasticity so that protrusion portion 252 may be spread to the outside of the main body housing 21.

In this case, the housing 210 is mounted on the main body housing 21 in the state in which the protrusion portion 252 is spread to the outside of the main body housing 21. In this case, as the protrusion portion 252 of the housing 210 is inserted and fixed into the groove portion 261 of the main body housing 21, the housing 210 may be coupled to the main body housing 21, and thus the shooting microstructure module 200 may be coupled to the applicator 20.

On the contrary, as the housing 210 is moved in a reverse direction to the main body housing 21 in the state in which the shooting microstructure module 200 is coupled to the applicator 20 and the protrusion portion 252 is spread to the outside of the main body housing 21, the housing 210 may be separated from the main body housing 21, and thus the shooting microstructure module 200 may be separated from the applicator 20.

Meanwhile, as a combination of the rotation coupling and the catching coupling, the groove portion 261 may have a "¬" shape. In this case, the groove portion 261 may include an extension portion vertically extending to one end of the main body housing 21. The protrusion portion 252 does not have elasticity.

In this case, when the housing 210 is rotated to one side of the main body housing 21 in the state in which the protrusion portion 252 is vertically inserted through the extension portion of the groove portion 261, the protrusion portion 252 may be rotated in a horizontal direction along the groove portion 261. As a result, the housing 210 may be coupled to the main body housing 21, and thus the shooting microstructure module 200 may be coupled to the applicator 20.

On the contrary, in the state in which the shooting microstructure module 200 is coupled to the applicator 20, the protrusion portion 252 is rotated in a reverse horizontal direction along the groove portion 261, and then the housing 210 is moved downward from the main body housing 21, such that the housing 210 may be separated from the main body housing 21, and thus the shooting microstructure module 200 may be separated from the applicator 20.

Figure 14:
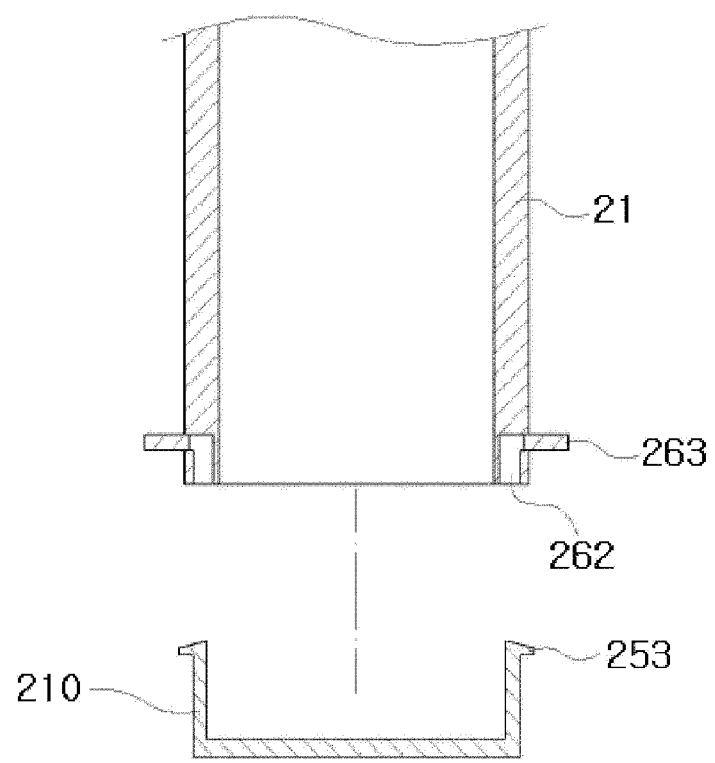
FIG. 14 is a cross-sectional view illustrating still another example in which the shooting microstructure module according to another exemplary embodiment of the present invention is coupled to the applicator.

FIG. 14 is a cross-sectional view illustrating still another example in which the shooting microstructure module according to the exemplary embodiment of the present invention is coupled to the applicator.

Referring to FIG. 14, the shooting microstructure module 200 and the applicator 20 may be coupled by insertion coupling. In this case, a groove portion 262, which is opened downward, may be formed at an end at one side of the main body housing 21. In this case, a push button 263 may be provided to communicate with the groove portion 262. The coupling member may include a hook member 253 provided at one end of the housing 210. In this case, the hook member 253 may have elasticity so as to be bent to one side.

In this case, when the hook member 253 of the housing 210 is inserted into the groove portion 262 of the main body housing 21, the hook member 253 is inserted and fixed into the groove portion 262, such that the housing 210 may be coupled to the main body housing 21, and thus the shooting microstructure module 200 may be coupled to the applicator 20.

On the contrary, when the push button 263 is pushed in the state in which the shooting microstructure module 200 is coupled to the applicator 20, the push button 263 is inserted into the groove portion 262 and pushes the hook member 253, such that the hook member 253 is bent to one side, and thus the hook member 253 may be separated from the groove portion 262. In this state, as the housing 210 is moved downward from the main body housing 21, the housing 210 may be separated from the main body housing 21, and thus the shooting microstructure module 200 may be separated from the applicator 20.

Meanwhile, instead of the groove portion 262 of the main body housing 21, a second hook member, which corresponds to the hook member 253, may be provided in the main body housing 21. In this case, the hook member 253 may have a push button provided at one side thereof. As another example, the second hook member may have a push button at one side thereof, and the push button may protrude outward from the main body housing 21.

In this case, when the housing 210 is pressed from below the main body housing 21, the hook member 350 is coupled to the second hook member in the main body housing 21, such that the housing 210 may be coupled to the main body housing 21, and thus the shooting microstructure module 200 may be coupled to the applicator 20.

On the contrary, when the push button provided on the hook member 253 or the push button provided on the second hook member is pushed in the state in which the shooting microstructure module 200 is coupled to the applicator 20, the corresponding push button presses and bends the hook member 253 or the second hook member to one side, such that the hook member 253 and the second hook member may be separated from each other. In this state, as the housing 210 is downward from the main body housing 21, the housing 210 may be separated from the main body housing 21, and thus the shooting microstructure module 200 may be separated from the applicator 20.

Comparative Example

Comparative Example shows an experimental result of measuring the coupling force between the perforated plate 110 and the base part 120 of the perforated plate microstructure module 100 according to the exemplary embodiment of the present invention by using the perforated plate 110 which is not subjected to the plasma surface treatment.

Experimental Example 1

Experimental Example 1 shows an experimental result of measuring the coupling force between the perforated plate 110 and the base part 120 of the perforated plate microstructure module 100 according to the exemplary embodiment of the present invention by using the perforated plate 110 on which the plasma surface treatment has performed for 1 minute.

Experimental Example 2

Experimental Example 2 shows an experimental result of measuring the coupling force between the perforated plate 110 and the base part 120 of the perforated plate microstructure module 100 according to the exemplary embodiment of the present invention by using the perforated plate 110 on which the plasma surface treatment has performed for 2 minutes.

Experimental Example 3

Experimental Example 3 shows an experimental result of measuring the coupling force between the perforated plate 110 and the base part 120 of the perforated plate microstructure module 100 according to the exemplary embodiment of the present invention by using the perforated plate 110 on which the plasma surface treatment has performed for 3 minutes.

Experimental Example 4

Experimental Example 4 shows an experimental result of measuring the coupling force between the perforated plate 110 and the base part 120 of the perforated plate microstructure module 100 according to the exemplary embodiment of the present invention by using the perforated plate 110 on which the plasma surface treatment has performed for 4 minutes.

Experimental Example 5

Experimental Example 5 shows an experimental result of measuring the coupling force between the perforated plate 110 and the base part 120 of the perforated plate microstructure module 100 according to the exemplary embodiment of the present invention by using the perforated plate 110 on which the plasma surface treatment has performed for 5 minutes.

In order to compare changes in coupling force between the perforated plate 110 and the base part 120 over plasma surface treatment time, Experimental Examples all have the same configuration in which the 69 openings 111 are formed in the perforated plate 110, and the experiments were performed under the condition in which the height of the base part 120 and the material of the perforated plate 110 remain the same.

The experiments measured the coupling force between the perforated plate 110 and the base part 120 by slowly applying external force to the perforated plate microstructure module 100 and measuring a peak value at the moment when the perforated plate 110 and the base part 120 are separated from each other.

TABLE 1

| Examples | Comparative Example | Experimental Example 1 | Experimental Example 2 | Experimental Example 3 | Experimental Example 4 | Experimental Example 5 |
|---|---|---|---|---|---|---|
| Plasma Surface Treatment Time (min) | 0 | 1 | 2 | 3 | 4 | 5 |
| Coupling Force (N) | 12.49 | 21.37 | 46.11 | 45.5 | 47.3 | 46.04 |

Figure 15:
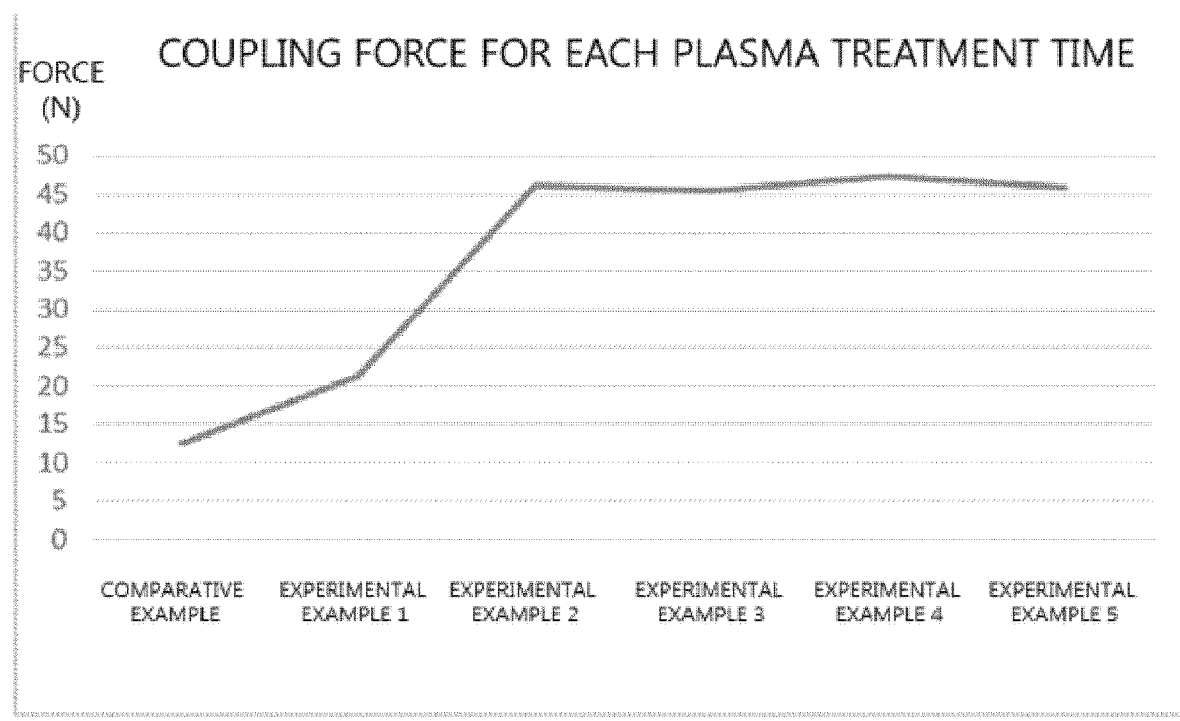
FIG. 15 is a graph illustrating experimental results of measuring coupling forces between perforated plates and base parts in a Comparative Example and Experimental Examples 1 to 5.

Table 1 and FIG. 15 are a table and a graph illustrating experimental results of measuring the coupling force between the perforated plate 110 and the base part 120 in a Comparative Example and Experimental Examples 1 to 5. Referring to Table 1 and FIG. 15, it can be seen that in the Comparative Example, the perforated plate 110 and the base part 120 were separated from each other when comparatively low force (12.49 N) was applied in comparison with Experimental Examples 1 to 5.

It can be seen that in Experimental Examples 2 to 5, the perforated plate 110 and the base part 120 were separated from each other when comparatively high force (45.5 N to 46.04 N) was applied in comparison with Experimental Example 1 in which the coupling force was 21.37 N.

Consequently, it can be seen that the coupling force between the perforated plate 110 and the base part 120 may be increased through the plasma surface treatment on the perforated plate 110. However, it can be seen that the coupling force between the perforated plate 110 and the base part 120 may be further increased when the plasma surface treatment on the perforated plate 110 continues for 1 minute or more, and the change in coupling force between the perforated plate 110 and the base part 120 is insignificant when the plasma surface treatment continues for 2 minutes or more.

<Coupling Force Experimental Data>

TABLE 2

| Experiment 1 (N) | | Experiment 2 (N) | |
|---|---|---|---|
| Example 1 | 0.8182 | Example 5 | 0.7680 |
| Example 2 | 0.8929 | Example 6 | 0.7032 |
| Example 3 | 0.8709 | Example 7 | 0.8841 |
| Example 4 | 1.0125 | Example 8 | 1.3101 |
| Average (A) (Example 1~4) | 0.8986 | Average (B) (Example 5~8) | 0.9163 |
| coupling force(B-A) 0.0177 N | | | |

<Experiment 1>

Experiment 1 shows an experimental result of measuring the pressing force. wherein the pressing force is the measured value when the pillar of the pressing member is inserted into the openings of the perforated plate.

<Experiment 2>

Experiment 2 shows an experimental result of measuring the pressing force. wherein the pressing force is the measured value when the pillar of the pressing member is inserted into the base part filling in the opening of the perforated plate.

In order to measure critical value of the coupling force between the perforated plate and the base parts, pressing force was measured when the pillar of the pressing member is inserted into the openings of the perforated plate.

The coupling force is calculated by the difference between the base part filling in the opening and the base parts being empty.

Table 2 is a table illustrating experiment results of measuring the pressing force when the pillar of the pressing member is inserted into the openings of the perforated plate.

Referring to Table 2, it can be seen that the base part and the perforated plate coupled are separable by force of at least 0.0177 N.

While the present invention has been described above with reference to the exemplary embodiments, it may be understood by those skilled in the art that the present invention may be variously modified and changed without departing from the spirit and scope of the present invention disclosed in the claims.

The invention claimed is:

1. A perforated plate microstructure module comprising:
   a housing on which an applicator detachably mounted on a first side;
   a perforated layer having a plurality of openings and positioned at a second side of the housing;
   a shooting microstructure provided on an upper part of the perforated layer in the housing and having a base part and a plurality of microstructure which formed on one surface of the base part corresponding to the openings; and
   a pressing member having a plate and a plurality of pillars formed on one surface of the plate;
   wherein the pressing member received in the first side of the housing and disposed at a certain height from the perforated layer, and
   wherein the pressing member shot to the perforated layer by the pressing force applied from the applicator, while the applicator is mounted on the housing,
   wherein the perforated layer has support parts which supporting the plate and formed around the openings, and
   wherein the plate has breakable catching parts provided at the positions corresponding to the support parts.

2. The perforated plate microstructure module according to claim 1, wherein the pillars have the same length or have different lengths at the outer and central portions of the plate.

3. The perforated plate microstructure module according to claim 1, wherein the catching parts are broken by the pressing applied to the plate.

4. The perforated plate microstructure module according to claim 1, wherein the catching parts have the shape and the size corresponding to a cross section of the support parts.

5. The perforated plate microstructure module according to claim 1, wherein the plate has through ports corresponding to a cross section of the support parts, and
wherein the catching parts provided in at least a part of the through ports.

6. The perforated plate microstructure module according to claim 1, wherein the housing has coupling members for coupling the housing to the applicator.

7. The perforated plate microstructure module according to claim 6, wherein the coupling members are configured by any one of rotation coupling, hook coupling, insertion coupling, catching coupling, magnetic coupling, and Velcro.

8. The perforated plate microstructure module according to claim 1, wherein the base part of the microstructure contains a biocompatible or biodegradable substance.

9. The perforated plate microstructure module according to claim 8, wherein the biocompatible or biodegradable substance is polyester, polyhydroxyalkanoate (PHAs), poly (α-hydroxyacid), poly(β-hydroxyacid), poly(3-hydroxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyether-ester, polyanhydride, poly(glycolic acid-co-trimethylene carbonate), polyphosphoester, polyphosphoester urethane, poly(amino acid), polycyanoacrylate, poly(trimethylene carbonate), poly(imino carbonate), poly(tyrosine carbonate), polycarbonate, poly(tyrosine arylate), polyalkylene oxalate, polyphosphazene, PHA-PEG, ethylene vinyl alcohol copolymer (EVOH), polyurethane, silicone, polyester, polyolefin, polyisobutylene and ethylene-alphaolefin copolymer, styrene-isobutylene-styrene triblock copolymer, acrylic polymer and copolymer, vinyl halide polymer and copolymer, polyvinyl chloride, polyvinyl ether, polyvinyl methyl ether, polyvinylidene halide, polyvinylidene fluoride, polyvinylidene chloride, polyfluoro alkene, polyperfluoroalkene, polyacrylonitrile, polyvinyl ketone, polyvinyl aromatics, polystyrene, polyvinyl ester, polyvinyl acetate, ethylene-methyl methacrylate copolymer, acrylonitrile-styrene copolymer, ABS resin and ethylene-vinyl acetate copolymer, polyamide, alkyd resin, polyoxymethylene, polyimide, polyether, polyacrylate, polymethacrylate, polyacrylic acid-co-maleic acid, chitosan, dextran, cellulose, heparin, hyaluronic acid, alginate, inulin, starch, or glycogen, and particularly, may contain one or more substances selected from polyester, polyhydroxyalkanoate (PHAs), poly(α-hydroxyacid), poly(β-hydroxyacid), poly(3-hydroxybutyrate-co-valerate; PHBV), poly(3-hydroxyproprionate; PHP), poly(3-hydroxyhexanoate; PHH), poly(4-hydroxyacid), poly(4-hydroxybutyrate), poly(4-hydroxyvalerate), poly(4-hydroxyhexanoate), poly(ester amide), polycaprolactone, polylactide, polyglycolide, poly(lactide-co-glycolide; PLGA), polydioxanone, polyorthoester, polyether ester, polyanhydride, poly(glycolic acid-co-trimethylene carbonate), polyphosphoester, polyphosphoester urethane, poly(amino acid), polycyano acrylate, poly(trimethylene carbonate), poly(imino carbonate), poly(tyrosine carbonate), polycarbonate, poly(tyrosine arylate), polyalkylene oxalate, polyphosphazene, PHA-PEG, chitosan, dextran, cellulose, heparin, hyaluronic acid, alginate, inulin, starch, glycogen and triamcinolone.

10. The perforated plate microstructure module according to claim 1, wherein the base part is 1% to 100% of a height of the perforated plate.

11. The perforated plate microstructure module according to claim 10, wherein the microstructure contains a medicinally active ingredient.

12. The perforated plate microstructure module according to claim 1, wherein the perforated plate or the base part is made of a hydrophilic material.

13. The perforated plate microstructure module according to claim 1, wherein the pillars and the base part are spaced apart by less than 1 cm.

14. An applicator for implanting a microstructure into the skin comprising:
a main body housing having a first side on which the perforated plate microstructure module of claim 1 mounted; and
a shooting member provided in the main body housing to press the pressing member,
wherein the perforated plate microstructure module has at least one coupling member for coupling the housing to the applicator.

15. The applicator of claim 14, wherein the shooting member comprising:
a piston which pressing the pressing member; and
a pushing member shoot the piston toward the pressing member.

16. The applicator of claim 14, wherein the main body housing has a screw thread formed along an outer circumference at the first side of the main body housing, and wherein the at least coupling member has a screw thread formed along an inner circumference at the first side of the housing.

17. The applicator of claim 14, wherein the main body housing has groove portions formed on an outer circumferential surface of the main body housing, and
wherein the at least one coupling member has protrusion portions formed at one end of the housing so as to correspond to the groove portion.

18. The applicator of claim 14, wherein the main body housing has groove portions formed at one end of the main body housing and push button provided to communicate with the groove portion, and
wherein the at least one coupling member has hook members formed at one end of the housing so as to correspond to the groove portion.

19. The applicator of claim 14, wherein the at least one coupling member has hook members provided at one end of the housing, and
wherein the main body housing has second hook members corresponding to the hook members in the main body housing.

* * * * *